(12) United States Patent
Kudo

(10) Patent No.: US 7,684,536 B2
(45) Date of Patent: Mar. 23, 2010

(54) RADIOGRAPHY APPARATUS AND RADIOGRAPHY METHOD

(75) Inventor: Masayuki Kudo, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 235 days.

(21) Appl. No.: 11/397,282

(22) Filed: Apr. 4, 2006

(65) Prior Publication Data

US 2006/0222142 A1    Oct. 5, 2006

(30) Foreign Application Priority Data

Apr. 5, 2005    (JP)    ............... 2005-108191

(51) Int. Cl.
*A61B 6/03*    (2006.01)
(52) U.S. Cl. ................. 378/8; 378/4; 378/62; 600/431
(58) Field of Classification Search .................... 378/4, 378/8, 62; 600/425, 431
See application file for complete search history.

(56) References Cited

U.S. PATENT DOCUMENTS

| | | | |
|---|---|---|---|
| 5,077,773 A | 12/1991 | Sammon | |
| 6,385,277 B1 | 5/2002 | Li | |
| 6,510,196 B2 | 1/2003 | Laner | |
| 6,947,584 B1 * | 9/2005 | Avila et al. | 382/131 |
| 6,990,172 B2 | 1/2006 | Toth et al. | |
| 2002/0054038 A1 * | 5/2002 | Nemoto | 345/419 |
| 2004/0111023 A1 * | 6/2004 | Edic et al. | 600/425 |
| 2005/0152493 A1 | 7/2005 | Seto | |
| 2005/0246120 A1 | 11/2005 | Hein | |

FOREIGN PATENT DOCUMENTS

| | | |
|---|---|---|
| JP | 2004-159983 | 6/2004 |
| JP | 2005-006772 | 1/2005 |

OTHER PUBLICATIONS

Tomandl et al., Comprehensive Imaging of Ischemic Stroke with Multisection CT, 2003, Radiographics, vol. 23, No. 3, pp. 565-592.*

(Continued)

*Primary Examiner*—Edward J Glick
*Assistant Examiner*—John M Corbett
(74) *Attorney, Agent, or Firm*—Armstrong Teasdale LLP

(57) ABSTRACT

The present invention attempts to reduce an amount of a contrast medium or a patient dose and improve diagnostic efficiency. The conditions for a main scan are designated so that a first scan of scanning a subject with a tube current of a first tube current value fed to an X-ray tube will be performed in order to examine the blood flow in a subject's blood vessel into which a contrast medium is injected. Moreover, the conditions for a main scan are designated so that a second scan of scanning the subject with a tube current of a second tube current value fed to the X-ray tube will be performed in order to image the subject's blood vessel into which the contrast medium is injected. Images of the subject are constructed based on projection data items produced by scanning the subject under the sets of conditions for a main scan.

20 Claims, 5 Drawing Sheets

OTHER PUBLICATIONS

Kaatee et al., Renal Artery Stenosis: Detection and Quantification with Spiral CT Angiography versus Optimized Digital Subtraction Angiography, 1997, Radiography, 205, pp. 121-127.*

Siemens AG, Somatom Volume Zoom Computed Tomography System for Volume Scanning, 2001, Order No. A91001-M2110-G138-06-7600, available at http://www.whoi.edu/science/B/csi/capabilities/scanner-specs.html.*

Hunter et al., Assessment of Cerebral Perfusion and Arterial Anatomy in Hyperacute Stroke with Three-dimensional Functional CT: Early Clinical Results, Jan. 1998, AJNR Am J Neuroradiol, vol. 19, pp. 29-37.*

Konig, Brain perfusion CT in acute stroke: current status, 2003, European Journal of Radiology, vol. 45, pp. S11-S22.*

Keat et al., GE LightSpeed16 CT Scanner Technical Evaluation, 2004, ISBN 1 84182 830 0.*

Platten et al., Sixteen slice CT scanner comparison report version 11, Jun. 2004, ISBN 1 84182 895 5.*

Ezzeddine et al., CT Angiography with Whole Brain Perfused Blood Volume Imaging, 2002, Stroke, vol. 33, pp. 959-966.*

Lev et al., Utility of Perfusion-Weighted CT Imaging in Acute Middle Cerebral Artery Stroke Treated with Intra-Arterial Thrombolysis, 2001, Stroke, vol. 32, pp. 2021-2028.*

Bernd F. Tomandl, et al., Comprehensive Imaging of Ischemic Stroke With Multisection CT, RadioGraphics May-Jun. 2003, vol. 23, No. 3, Education Exhibit, pp. 565-592.

European Search Report and Opinion, European Patent Office, Reference 180173/11390, Appln. No. 06251682.8-2305, Date of completion of search Jul. 20, 2006, 11 pgs.

Comprehensive Imaging of Ischemic Stroke with Multisection CT, Bernd F. Tomandl, MD, et al., Radio Graphics, vol. 23, No. 3, pp. 565-592, dated May-Jun. 2003, Japan.

Usefulness of Perfusion Study on Head Assisted by 3D-CTA, Tatsuya Sato, Medical Journal of Niigata Prefectural Koide Hospital, vol. 7, pp. 20-23, dated May 15, 2004, Japan.

Usefulness of CT-Perfusion in Acute Cerebral Infarction, Hiroyuki Yamamoto, Kurashiki Central Hospital Radiology Center, pp. 1580-1585, dated Nov. 4, 2003, Japan.

* cited by examiner

RADIOGRAPHY APPARATUS AND RADIOGRAPHY METHOD

CROSS REFERENCE TO RELATED APPLICATIONS

This application claims the benefit of Japanese Application No. 2005-108191 filed Apr. 5, 2005.

BACKGROUND OF THE INVENTION

The present invention relates to a radiography apparatus and a radiography method. More particularly, the present invention is concerned with a radiography apparatus and a radiography method which construct images of a subject according to projection data items of the subject produced by performing a main scan in which radiation is irradiated from a radiation tube to the subject and radiation transmitted by the subject is detected.

A radiography apparatus including an X-ray computed tomography (CT) apparatus reconstructs images of a subject's tomographic layer according to projection data items produced by scanning a subject with radiation. The radiography apparatus is widely adopted for medical application and industrial application.

In the radiography apparatus, for example, a blood flow examination called CT perfusion or angiography called CT angiography is performed using a contrast medium for the purpose of diagnosis of an ischemic disease in an encephalic region (refer to, for example, Patent Document 1 and Patent Document 2).

[Patent Document 1] Japanese Unexamined Patent Publication No. 2004-159983

[Patent Document 2] Japanese Unexamined Patent Publication No. 2005-6772

For CT perfusion or CT angiography, a scan is performed exclusively to each of CT perfusion and CT angiography in order to acquire data concerning a blood flow examination or data concerning images constructed through angiography.

Therefore, it may be hard to minimize an amount of a contrast medium or a patient dose. Moreover, since an examination lasts over a long period of time, it may be hard to improve diagnostic efficiency.

SUMMARY OF THE INVENTION

Therefore, an object of the present invention is to provide a radiography apparatus and a radiography method which make it easy to minimize an amount of a contrast medium or a patient dose and make it possible to improve diagnostic efficiency.

In efforts to accomplish the above object, according to the present invention, there is provided a radiography apparatus that constructs images of a subject according to projection data items of the subject produced by performing a main scan in which radiography is irradiated to the subject and radiography transmitted by the subject is detected. The radiography apparatus includes: a conditions-for-main scan designation unit that designates the conditions for a main scan; a radiation tube that irradiates radiation to a subject according to the conditions for a main scan designated by the conditions-for-main scan designation unit; and a detection unit that has a plurality of detection elements, each of which detects radiation irradiated from the radiation tube and transmitted by the subject so as to produce projection data, the plurality of detection elements being arranged in array form. The conditions-for-main scan designation unit designates the conditions for a main scan so that a first scan of scanning the subject with a tube current of a first tube current value fed to the radiation tube, and a second scan of scanning the subject with a tube current of a second tube current value different from the first tube current value fed to the radiation tube will be performed successively. The radiation tube irradiates radiation to the subject so that the first scan and second scan will be successively performed under the conditions for a main scan designated by the conditions-for-main scan designation unit.

In efforts to accomplish the foregoing object, according to the present invention, there is provided a radiography method for constructing images of a subject according to projection data items of the subject produced by performing a main scan in which radiation is irradiated from a radiation tube to the subject and radiation transmitted by the subject is detected. The radiography method includes a first step of designating the conditions for a main scan, and a second step of constructing images of a subject according to projection data items produced by scanning the subject according to the conditions for a main scan designated at the first step. At the first step, a first scan of scanning the subject with a tube current of a first tube current value fed to the radiation tube and a second scan of scanning the subject with a tube current of a second tube current value different from the first tube current value fed to the subject are performed successively.

According to the present invention, there are provided a radiography apparatus and a radiography method which make it easy to reduce an amount of a contrast medium or a patient dose and make it possible to improve diagnostic efficiency.

Further objects and advantages of the present invention will be apparent from the following description of the preferred embodiments of the invention as illustrated in the accompanying drawings.

DETAILED DESCRIPTION OF THE INVENTION

An embodiment of the present invention will be described below.

Figure 1:
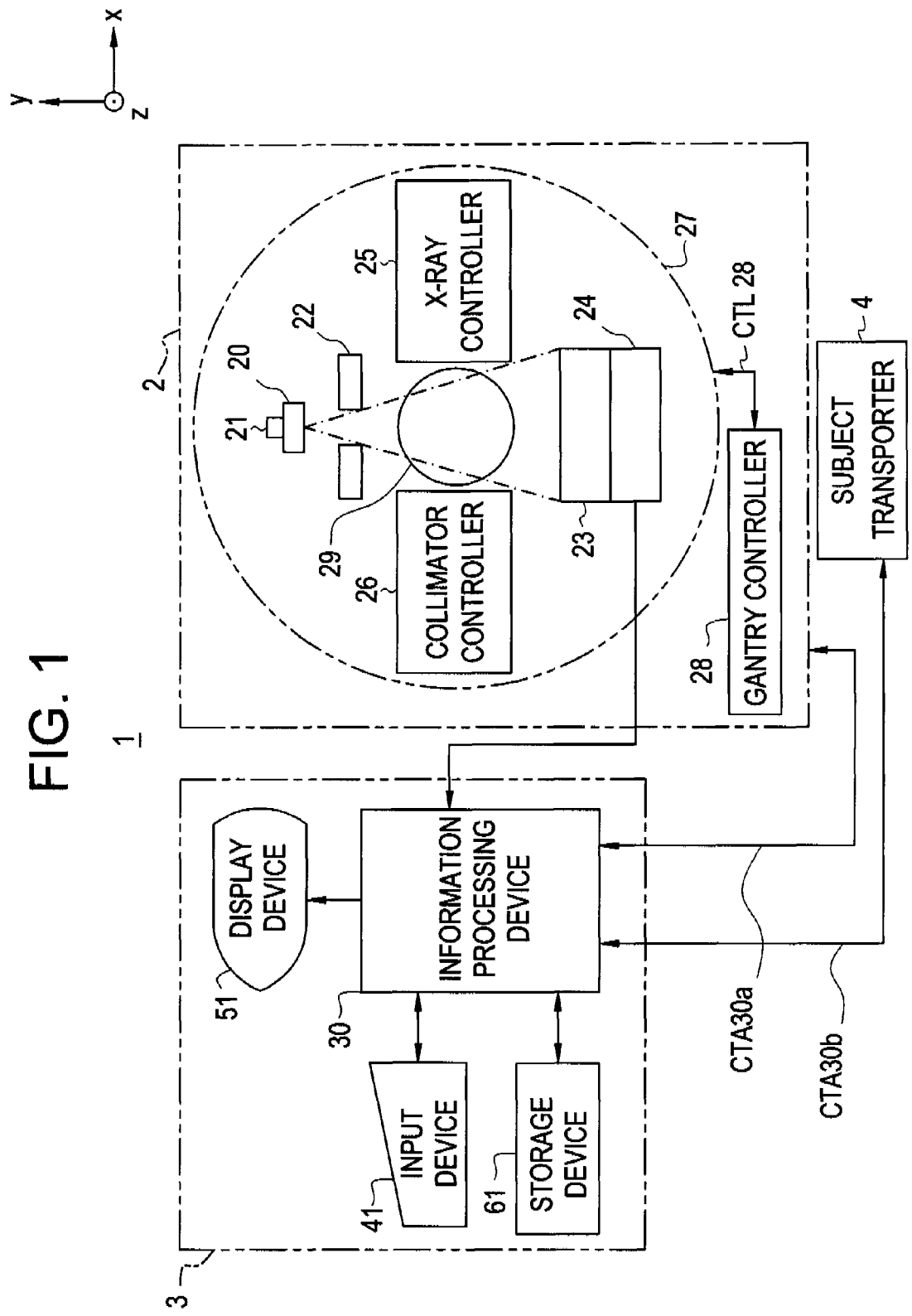
FIG. 1 is a block diagram showing the overall configuration of an X-ray CT apparatus in accordance with an embodiment of the present invention.
Figure 2:
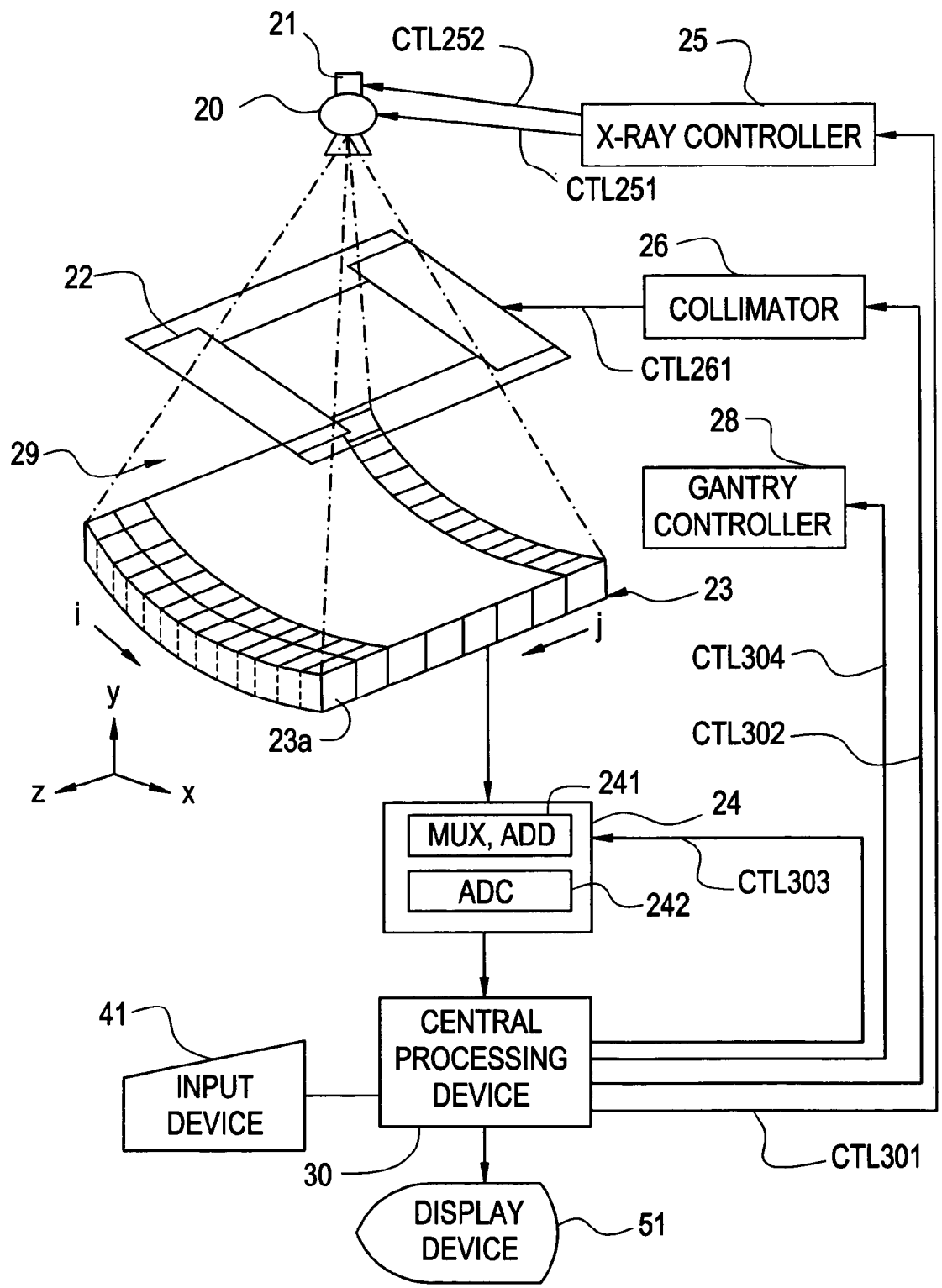
FIG. 2 shows the configuration of a major portion of the X-ray CT apparatus in accordance with the embodiment of the present invention.

FIG. 1 is a block diagram showing the overall configuration of an X-ray CT apparatus 1 in accordance with an embodiment of the present invention. FIG. 2 shows the configuration of a major portion of the X-ray CT apparatus 1 in accordance with the embodiment.

As shown in FIG. 1, the X-ray CT apparatus 1 includes a scanner gantry 2, an operator console 3, and a subject transporter 4. The X-ray CT apparatus 1 uses projection data items of a subject, which are produced by scanning the subject with X-rays according to the conditions for a scan, to reconstruct images of the subject's tomographic layer.

The scanner gantry 2 will be described below.

The scanner gantry 2 scans a subject, who is moved to an imaging space 29 by the subject transporter 4, according to a control signal CTL30a sent from the operator console 3, and produces projection data items of the subject. The scanner gantry 2 includes, as shown in FIG. 1, an X-ray tube 20, an X-ray tube mover 21, a collimator 22, an X-ray detector 23, a data acquisition unit 24, an X-ray controller 25, a collimator controller 26, a rotator 27, and a gantry controller 28. In the scanner gantry 2, as shown in FIG. 2, the X-ray tube 20 and X-ray detector 23 are disposed with the imaging space 29, into which a subject is carried, between them. The collimator 22 is disposed to reshape X-rays irradiated from the X-ray tube 20 to the subject lying in the imaging space 29. The scanner gantry 2 causes the X-ray tube 20, collimator 22, and X-ray detector 23 to turn about the subject with the direction z of the subject's body axis as a center. Consequently, the X-ray tube 20 radiates X-rays from a plurality of directions, in which respective views are produced, around the subject, and the X-ray detector 23 detects X-rays irradiated from the X-ray tube 20 and transmitted by the subject so as to produce projection data items. The components of the scanner gantry 2 will be successively described below.

The X-ray tube 20 is, for example, of a rotating anode type and irradiates X-rays to a subject. As shown in FIG. 2, the X-ray tube 20 irradiates X-rays of a predetermined intensity to a subject's region to be imaged via the collimator 22 according to a control signal CTL251 sent from the X-ray controller 25. X-rays radiated from the X-ray tube 20 are reshaped into, for example, a conical shape by the collimator 22, and then irradiated to the X-ray detector 23. The X-ray tube 20 is rotated about a subject by the rotator 27 with the direction z of the subject's body axis as a center in order to irradiate X-rays to the subject from directions, in which respective views are produced, around the subject. Namely, the X-ray tube 20 is turned about a subject with an axis, which extends in a direction in which the subject transporter 4 moves to carry the subject into the imaging space 29, as a center.

The X-ray tube mover 21 moves, as shown in FIG. 2, the radiant center of the X-ray tube in the direction z of the subject's body axis within the imaging space 29 of the scanner gantry 2 according to a control signal CTL252 sent from the X-ray controller 25.

The collimator 22 is, as shown in FIG. 2, interposed between the X-ray tube 20 and the X-ray detector 23. The collimator 22 has, for example, shielding plates, which do not transmit X-rays, arranged in twos in the direction of channels i and the direction of arrays j. The collimator 22 moves the two shielding plates, which are arranged in each of the directions, independently of each other according to a control signal CTL261 sent from the collimator controller 26, and thus intercepts X-rays radiated from the X-ray tube 20 in the respective directions so as to conically reshape the X-rays. Thus, a range of X-irradiation is adjusted. Namely, the collimator 22 varies the size of an opening, through which X-rays radiated from the X-ray tube 20 pass, so as to adjust the range of X-irradiation.

The X-ray detector 23 detects X-rays radiated from the X-ray tube 20 and transmitted by a subject so as to produce projection data items of the subject. The X-ray detector 23 is rotated about the subject together with the X-ray tube 20 by means of the rotator 27. The X-ray detector 23 then detects X-rays, which are radiated from the X-ray tube 20 and transmitted by the subject, around the subject so as to produce projection data items.

As shown in FIG. 2, the X-ray detector 23 includes a plurality of detector elements 23a. The X-ray detector 23 has the detector elements 23a two-dimensionally set in array in a direction of channels i corresponding to a direction of rotation in which the X-ray tube 20 is rotated about a subject in the imaging space 29 by means of the rotator 27, and a direction of arrays j corresponding to the direction of an axis of rotation serving as a center axis about which the X-ray tube 20 is rotated by the rotator 27. For example, the X-ray detector 23 has about one thousand detector elements 23a juxtaposed in the direction of channels i and has about thirty-two to sixty-four detector elements juxtaposed in the direction of arrays j. Moreover, the X-ray detector 23 has the face thereof curved like a cylindrical concave surface owing to the plurality of two-dimensionally arrayed detector elements 23a.

The detector elements 23a constituting the X-ray detector 23 are constructed as solid-state detectors each including a scintillator (not shown) that converts X-rays into light and a photodiode (not shown) that converts light produced by the scintillator into charge. However, the detector element 23a is not limited to the solid-state detector but may be a semiconductor detector element utilizing cadmium telluride or an ion chamber type detector element utilizing xenon gas.

The data acquisition unit 24 is included for acquiring projection data items produced by the X-ray detector 23. The data acquisition unit 24 acquires projection data items produced from X-rays detected by the detector elements 23a constituting the X-ray detector 23, and transmits the projection data items to the operator console 3. As shown in FIG. 2, the data acquisition unit 24 includes a selection/addition switching circuit (MUX,ADD) 241 and an analog-to-digital converter (ADC) 242. The selection/addition switching circuit 241 selects some of projection data items, which are produced from X-rays detected by the detector elements 23a constituting the X-ray detector 23, according to a control signal CTL303 sent from an information processing device 30, or summates any set of projection data items, and then transfers the resultant projection data items or projection data to the analog-to-digital converter 242. The analog-to-digital converter 242 converts projection data, which is selected or calculated by summating an arbitrary set of projection data items by means of the selection/addition switching circuit 241, from an analog signal to a digital signal, and then transfers the resultant signal to the information processing device 30.

The X-ray controller 25 transmits, as shown in FIG. 2, a control signal CTL251 to the X-ray tube 20 according to a control signal CTL301 sent from the information processing device 30, thus controlling X-irradiation. The X-ray controller 25 controls, for example, a tube current of the X-ray tube 20 or an irradiation time. Moreover, the X-ray controller 25 transmits a control signal CTL252 to the X-ray tube mover 21 according to a control signal CTL301 sent from the information processing device 30, and thus controls the X-ray tube 20 so as to move the radiant center of the X-ray tube 20 in the body-axis direction z.

The collimator controller 26 transmits, as shown in FIG. 2, a control signal CTL261 to the collimator 22 according to a control signal CTL302 sent from the information processing device 30, and thus controls the collimator 22 so that the collimator 22 will reshape X-rays irradiated from the X-ray tube 20 to a subject.

The rotator 27 is, as shown in FIG. 1, cylindrical and has the imaging space 29 formed in the center thereof. The rotator 27 drives, for example, a motor (not shown) according to a control signal CTL28 sent from the gantry controller 28 so as to rotate with the direction z of a subject's body axis in the imaging space 29 as a center. The rotator 27 accommodates the X-ray tube 20, X-ray tube mover 21, collimator 22, X-ray detector 23, data acquisition unit 24, X-ray controller 25, and collimator controller 26. The rotator 27 supplies power to these components via a slip ring (not shown). The rotator 27 rotates the components about a subject and changes the positional relationships of the components to the subject, who is carried into the imaging space 29, relatively in the direction of rotation. The rotation of the rotator 27 permits the X-ray tube 20 to irradiate X-rays to a subject in each of a plurality of directions, in which respective views are produced, around the subject. Consequently, the X-ray detector 23 can detect X-rays transmitted by the subject in each of the directions in which respective views are produced.

The gantry controller 28 transmits, as shown in FIG. 1 and FIG. 2, a control signal CTL28 to the rotator 27 according to a control signal CTL304 sent from the information processing device 30 included in the operator console 3. The gantry controller 28 thus controls the rotator 27 so that the rotator 27 will rotate.

The operator console 3 will be described below.

The operator console 3 includes, as shown in FIG. 1, the information processing device 30, an input device 41, a display device 51, and a storage device 61. These components will be described successively.

The information processing device 30 included in the operator console 3 performs various pieces of processing in response to a command which an operator enters at the input device 41. The information processing device 30 includes a computer and programs that cause the computer to function as various pieces of means.

Figure 3:
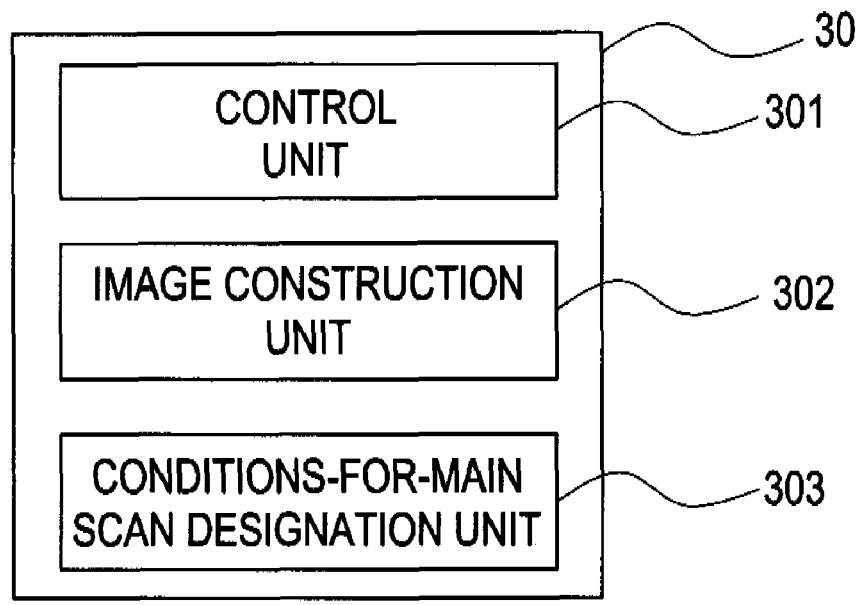
FIG. 3 is a block diagram showing the configuration of an information processing device included in the embodiment of the present invention.

FIG. 3 is a block diagram showing the configuration of the information processing device 30.

The information processing device 30 includes, as shown in FIG. 3, a control unit 301, an image construction unit 302, and a conditions-for-main scan designation unit 303. These components include programs that cause the computer to function as various pieces of means.

The control unit 301 is included for controlling the components of the X-ray CT apparatus 1. The control unit 301 controls the components in response to a command which an operator enters at the input device 41. For example, the control unit 301 controls the components according to the conditions for a main scan designated by the conditions-for-main scan designation unit 303, and performs a main scan. Specifically, the control unit 301 transmits a control signal CTL30b to the subject transporter 4, and thus causes the subject transporter 4 to transport a subject to the imaging space 29. The control unit 301 then transmits a control signal CTL304 to the gantry controller 28, and thus causes the gantry controller 28 to rotate the rotator 27 included in the scanner gantry 2. The control unit 301 transmits a control signal CTL301 to the X-ray controller 25 so that X-rays will be irradiated from the X-ray tube 20. The control unit 301 then transmits a control signal CTL302 to the collimator 26, and thus controls the collimator 22 so that the collimator will reshape X-rays. The control unit 301 transmits a control signal CTL303 to the data acquisition unit 24, and thus controls the data acquisition unit 24 so that the data acquisition unit will acquire projection data items produced by the detector elements 23a constituting the X-ray detector 23.

According to the present embodiment, the control unit 301 controls the components of the X-ray CT apparatus so that CT perfusion and CT angiography will be successively performed on the subject's brain under the conditions for a main scan designated by the conditions-for-main scan designation unit 303. Herein, the control unit 301 controls the components so that a first scan of scanning a subject with a tube current of a first tube current value fed to the X-ray tube 20 will be time-sequentially continuously performed in order to achieve CT perfusion that is an examination made of the blood flow in a subject's vessel into which a contrast medium is injected. Thereafter, the control unit 301 controls the components so that a second scan of scanning a subject with a tube current of a second tube current value larger than the first tube current value fed to the X-ray tube 20 will be performed in order to achieve CT angiography that is a kind of radiography for imaging the subject's blood vessel into which the contrast medium is injected. Herein, the control unit 301 controls the components so that the first scan intended for CT perfusion will be performed in a cine scan mode and the second scan intended for CT angiography will be performed in the cine mode. Thus, the control unit 301 controls the components so that the scans will be performed on the same position on a subject in the same scan mode under a plurality of sets of conditions for a scan.

The image construction unit 302 constructs images of a subject according to projection data items acquired by the data acquisition unit 24.

According to the present embodiment, the image construction unit 302 constructs perfusion images of a subject according to projection data items produced by performing the first scan intended for CT perfusion. Herein, first, projection data items produced by performing the first scan are used to reconstruct images of a subject's tomographic layer according to a filtering back projection method or any other image reconstruction method. Information on time-sequential changes in CT numbers is acquired from the images. Namely, a time-vs.-concentration curve is plotted. The time-vs.-concentration curve is analyzed in order to construct perfusion images providing pieces of information on the kinetics of a blood flow, such as, a cerebral blood flow (CBF), a cerebral blood volume (CBV), and a mean transit time (MTT).

According to the present embodiment, the image construction unit 302 constructs images of subject's blood vessels according to projection data items produced by performing the second scan intended for CT angiography. For example, the image construction unit 302 renders the blood vessels according to the projection data items produced by performing the second scan, and thus constructs a three-dimensional image representing the subject's blood vessels. The image construction unit 302 constructs as the three-dimensional image a surface-rendering image, a volume-rendering image, or an MIP image.

The conditions-for-main scan designation unit 303 designates the conditions for a main scan in which X-rays are irradiated to a subject and X-rays transmitted by the subject are detected. For example, the conditions-for-main scan designation unit 303 designates the conditions for a scan including a scan mode, a tube current value, a scan time, and a slice thickness. The conditions-for-main scan designation unit 303 transmits data of the designated conditions for a scan to the control unit 301, whereby the components are controlled.

According to the present embodiment, the conditions-for-main scan designation unit 303 designates the conditions for a main scan in response to a command which an operator enters at the input device 41, so that CT perfusion and CT angiography will be successively performed on a subject's brain. Specifically, the conditions-for-main scan designation unit 303 designates the conditions for a main scan so that a first scan of scanning a subject with a tube current of a first tube current value fed to the X-ray tube 20 will be time-sequentially continuously performed in order to achieve CT perfusion that is an examination of a blood flow in a subject's vessel into which a contrast medium is injected. Herein, the conditions-for-main scan designation unit 303 designates a cine scan mode so that the first scan intended for CT perfusion will be performed in the cine scan mode. Thereafter, the conditions-for-main scan designation unit 303 designates the conditions for a main scan so that a second scan of scanning a subject with a tube current of a second tube current value larger than the first tube current value fed to the X-ray tube 20 will be performed in order to achieve CT angiography that is a kind of radiography for imaging the subject's blood vessel into which the contrast medium is injected. Herein, the conditions-for-main scan designation unit 303 designates the cine scan mode so that the second scan intended for CT angiography will be performed in the cine scan mode. Thus, scans are performed on the same position on a subject in the same scan mode under a plurality of sets of conditions for a scan.

The input device 41 included in the operator console 3 is composed of, for example, a keyboard and a mouse. The input device 41 transfers various pieces of information including the conditions for a scan and information on a subject or various commands to the information processing device 30 responsively to an operator's manipulation performed on the input device. The input device 41 receives a command which instructs initiation of a main scan and which is entered by an operator.

The display device 51 included in the operator console 3 has, for example, a cathode-ray tube (CRT), and displays an image on a display surface thereof in response to a command sent from the information processing device 30. According to the present embodiment, the display device 51 time-sequentially displays perfusion images, which are constructed by the image construction unit 302, in real time. Moreover, the display device 51 displays on the display surface a three-dimensional image, which represents subject's blood vessels and is constructed by the image construction unit 302, by the side of the perfusion images.

The storage device 61 included in the operator console 3 includes a memory. Programs and other data are stored in the storage device 61. The storage device 61 has the stored data accessed by the information processing device 30 if necessary.

The subject transporter 4 will be described below.

The subject transporter 4 transports a subject between the inside of the imaging space 29 and the outside thereof.

Figure 4:
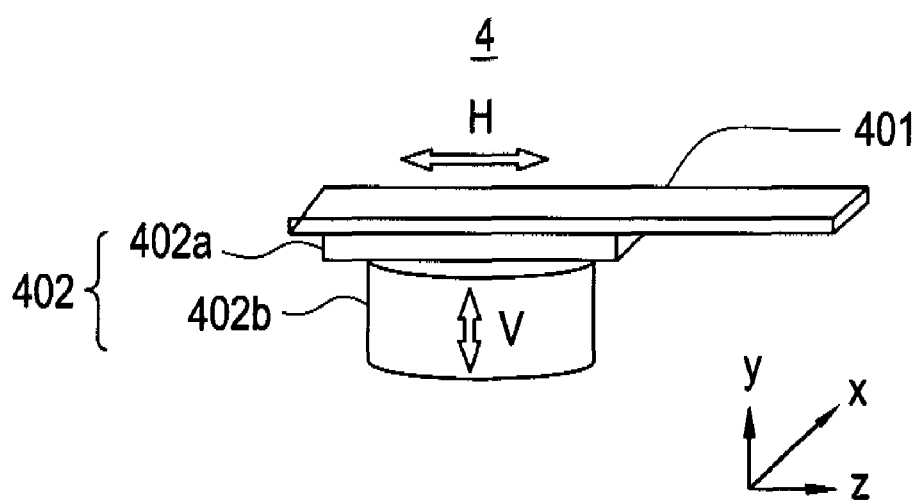
FIG. 4 is a perspective view showing the construction of a subject transporter included in the embodiment of the present invention.

FIG. 4 is a perspective view showing the configuration of the subject transporter 4.

As shown in FIG. 4, the subject transporter 4 includes a table 401 and a table mover 402.

The table 401 included in the subject transporter 4 has a placement surface on which a subject lies down and which bears the subject. For example, the subject lies down supinely on the table, and is thus borne by the table 401 included in the subject transporter 4.

The table mover 402 included in the subject transporter 4 includes a horizontal mover 402a that moves the table 401 in horizontal directions H one of which corresponds to the direction z of a subject's body axis, and a vertical mover 402b that moves the table 401 in vertical directions V perpendicular to the horizontal directions H. Based on a control signal CTL30b sent from the information processing device 30, the table mover 402 moves the table 401 so that a subject will be transported to the inside of the imaging space 29.

According to the present embodiment, the X-ray CT apparatus 1 is equivalent to a radiography apparatus in accordance with the present invention. The X-ray tube 20 included in the present embodiment is equivalent to a radiation tube employed in the present invention. Moreover, the X-ray detector 23 included in the present embodiment is equivalent to a detection unit employed in the present invention. The detector elements 23a included in the present embodiment are equivalent to detection elements employed in the present invention. Moreover, the display device 51 included in the present embodiment is equivalent to a display unit employed in the present invention. The image construction unit 302 included in the present embodiment is equivalent to an image construction unit employed in the present invention. The conditions-for-main scan designation unit 303 included in the present embodiment is equivalent to a conditions-for-main scan designation unit employed in the present invention.

Actions to be performed in the X-ray CT apparatus 1 in accordance with the present embodiment will be described below.

Figure 5:
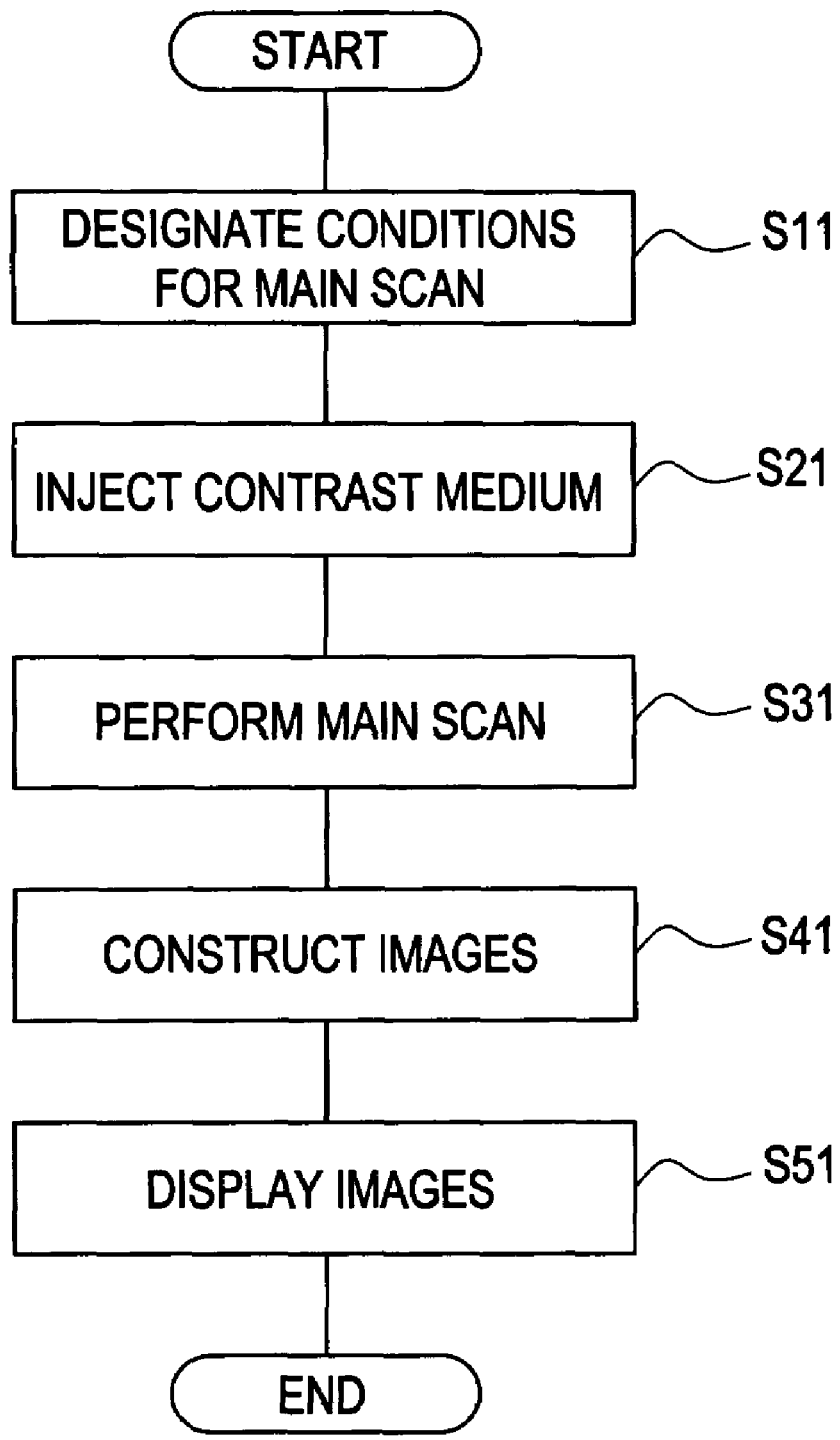
FIG. 5 is a flowchart describing major actions to be performed during a main scan of a subject in the embodiment of the present invention.

FIG. 5 is a flowchart describing major actions to be performed for a main scan of a subject.

As shown in FIG. 5, first, the conditions for a main scan are designated (S11).

Herein, the conditions-for-main scan designation unit 303 designates the conditions for a scan including a scan mode, a tube current value, a scan time, a slice position, a slice thickness, and the width of an X-ray beam in response to a command which an operator enters at the input device 41. According to the present embodiment, the conditions for a main scan are designated so that CT perfusion and CT angiography will be successively performed on a subject's brain.

Figure 6:
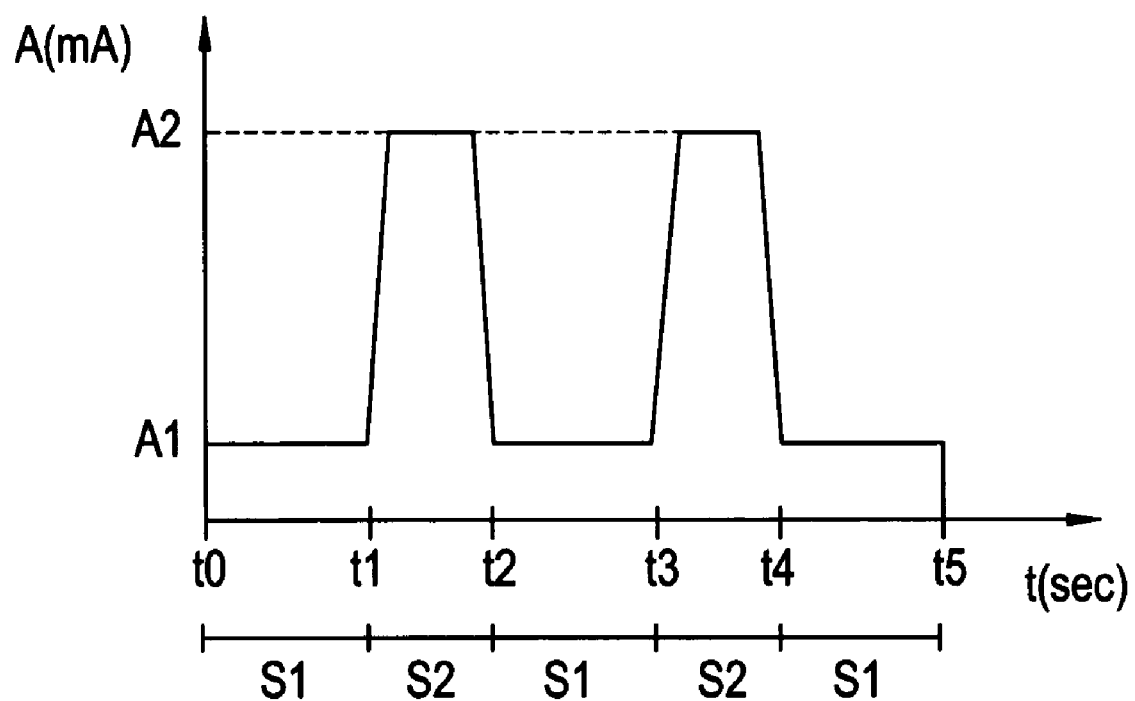
FIG. 6 graphically shows one of the conditions for a main scan designated in the embodiment of the present invention.

FIG. 6 graphically shows one of the conditions for a main scan designated in the present embodiment. In FIG. 6, the axis of abscissas indicates times t (seconds), and the axis of ordinates indicates tube current values A (mA).

As shown in FIG. 6, during a period from a main scan start time instant t0, which succeeds the elapse of a predetermined time from the instant a contrast medium is injected into a subject, to a time instant t1, a first scan S1 of scanning a subject with a tube current of a first tube current value A1 fed to the X-ray tube 20 is scheduled to be time-sequentially continuously performed in order to achieve CT perfusion that is an examination of a blood flow in a subject's blood vessel into which the contrast medium in injected. For example, the tube current is set to a value of 40 mA. Herein, the conditions-for-main scan designation unit 303 designates a cine scan mode for the first scan S1.

Thereafter, during a period from the time instant t1 to a time instant t2, a second scan S2 of scanning a subject with a tube current of a second tube current value A2 larger than the first tube current value A1 fed to the X-ray tube 20 is scheduled to be performed in order to achieve CT angiography that is a kind of radiography for imaging the subject's blood vessel into which the contrast medium is injected. For example, the tube current is set to a value of 200 mA. Herein, the conditions-for-main scan designation unit 303 designates a cine scan mode and a scan time of about 2 sec for the second scan S2.

Thereafter, during a period from a time instant t2 to a time instant t3, the first scan is scheduled to be performed under the foregoing conditions. During a period from the time instant t3 to a time instant t4, the second scan is scheduled to be performed under the foregoing conditions. During a period from the time instant t4 to a main scan end time instant t5, the first scan is scheduled to be performed again. At the main scan end time instant t5, the main scan is scheduled to be terminated.

Thereafter, a contrast medium is injected into the subject (S21).

Herein, a contrast medium is injected into a subject's blood vessel in consideration of a subject's region to be imaged. For example, an automatic contrast medium injector (not shown) is used to inject a predetermined amount of an iodine contrast medium into a subject at a certain rate.

Next, a main scan is performed (S31).

Herein, the control unit 301 controls the components of the X-ray CT apparatus so that CT perfusion and CT angiography will be successively performed on a subject's brain according to the conditions for a main scan designated by the conditions-for-main scan designation unit 303.

Specifically, as described in conjunction with FIG. 6, during the period from the main scan start time instant t0, which succeeds the elapse of a predetermined time from the instant the contrast medium is injected into the subject, to the time instant t1, the first scan S1 of scanning the subject with a tube current of the first tube current value A1 fed to the X-ray tube 20 is time-sequentially continuously performed in the cine scan mode. Thereafter, during the period from the time instant t1 to the time instant t2, the second scan S2 of scanning the subject with a tube current of the second tube current value A2 larger than the first tube current value A1 fed to the X-ray tube 20 is performed in the cine scan mode. Thereafter, during the period from the time instant t2 to the time instant t3, the first scan is performed under the foregoing designated conditions. During the period from the time instant t3 to the time instant t4, the second scan is performed under the foregoing designated conditions. During the period from the time instant t4 to the main scan end time instant t5, the first scan is performed again. The main scan is terminated at the main scan end time instant t5.

Thereafter, images of the subject are constructed (S41).

Herein, the image construction unit 302 constructs images of the subject according to projection data items produced by performing the main scan and acquired by the data acquisition unit 24. In the present embodiment, as shown in FIG. 6, during the period from the main scan start time instant t0 to the time instant t1, the image construction unit 302 constructs perfusion images of the subject according to projection data items produced by performing the first scan S1 for CT perfusion. For example, a plurality of perfusion images providing pieces of information on a cerebral blood flow (CBF), a cerebral blood volume (CBV), and a mean transit time (MTT) respectively are constructed in real time with the first scan S1. During the period from the time instant t1 to the time instant t2, a three-dimensional image representing subject's blood vessels is constructed based on projection data items, which are produced by performing the second scan for CT angiography, in real time with the second scan. For example, a volume-rendering image is constructed as the three-dimensional image. Even during the period from the time instant t2 to the time instant t3, the period from the time instant t3 to the time instant t4, and the period from the time instant t4 to the main scan end time instant t5, the image construction unit 302 constructs images of the subject according to the conditions for a scan in the same manner.

Thereafter, the images of the subject are displayed (S51).

Herein, the images of the subject constructed by the image construction unit 302 are displayed on the display surface of the display device 51. In the present embodiment, as shown in FIG. 6, during the period from the main scan start time instant t0 to the time instant t1, the perfusion images constructed by the image construction unit 302 are displayed on the display device 51. For example, the plurality of perfusion images providing the pieces of information on the CBF, CBV, and MTT is displayed side by side on the display surface in real time with the first scan S1. During the period from the time instant t1 to the time instant t2, the three-dimensional image representing the subject's blood vessels and being constructed by the image construction unit 302 is displayed in real time with the second scan. For example, a volume-rendering image is displayed as the three-dimensional image. Even during the period from the time instant t2 to the time instant t3, the period from the time instant t3 to the time instant t4, and the period from the time instant t4 to the main scan end time instant t5, the images of the subject constructed by the image construction unit 302 are displayed on the display device 51 in the same manner.

As mentioned above, according to the present embodiment, the conditions for a main scan are designated so that a first scan of scanning a subject with a tube current of a first tube current value fed to the X-ray tube 20 and a second scan of scanning the subject with a tube current of a second tube current value A2 different from the first tube current value A1 fed to the X-ray tube 20 are successively performed. Herein, the conditions for a main scan are designated so that the first scan of scanning a subject with the tube current of the first tube current value A1 fed to the X-ray tube 20 will be performed in order to examine the blood flow in a subject's blood vessel into which a contrast medium is injected. Moreover, the conditions for a main scan are designated so that the second scan of scanning a subject with the tube current of the second tube current value A2 fed to the X-ray tube 20 will be performed in order to image the subject's blood vessel into which the contrast medium is injected. Images of the subject are constructed based on projection data items produced by scanning the subject under the conditions for a main scan. Thus, according to the present embodiment, CT perfusion and CT angiography are successively performed on a subject's brain according to the different sets of conditions for a main scan designated by the conditions-for-main scan designation unit 303. It is therefore easy to reduce an amount of a contrast medium and a patient dose. Moreover, one scan provides images that may be used for different purposes. This leads to improvement of diagnostic efficiency.

Noted is that the present invention will not be limited to the foregoing embodiment. Various variants may be adopted.

For example, according to the aforesaid embodiment, X-rays are used as radiation. The present invention is not limited to X-rays. Alternatively, for example, gamma rays or any other radiation may be adopted.

For example, according to the aforesaid embodiment, the timing of switching the first scan S1 to the second scan S2 is designated in response to a command which an operator enters. The present invention is not limited to this mode. Alternatively, for example, a monitor scan for monitoring a contrast medium injected into a subject's body may be performed prior to a main scan, and the timing of switching the first scan S1 into the second scan S2 may be designated based on CT numbers of pixels within a range representing a region of interest in an image constructed based on data acquired through the monitor scan. In other words, the timing of switching the first scan S1 into the second scan S2 may be set to a time instant at which the CT numbers of pixels within the range representing a region of interest in an image resulting from a so-called SmartPrep technique reach a reference value.

According to the aforesaid embodiment, the first scan S1 and second scan S2 are performed in the cine scan mode. The present invention is not limited to the scan mode. Alternatively, the first scan and second scan may be performed in an axial scan mode.

Many widely different embodiments of the invention may be configured without departing from the spirit and the scope of the present invention. It should be understood that the present invention is not limited to the specific embodiments described in the specification, except as defined in the appended claims.

The invention claimed is:

1. A radiography apparatus for producing a time-sequentially continuous plurality of images of a subject using projection data items of the subject obtained by performing a single main scan by which a radiation irradiated to the subject and transmitted through the subject is detected, said radiographic apparatus comprising:
   a conditions-for-main scan designation device for designating the conditions for the single main scan that is staffed after a contrast medium is injected into a blood vessel of the subject, the single main scan producing the time-sequentially continuous plurality of images at one position;
   a radiation tube for irradiating radiation to the subject during the single main scan according to the conditions designated by said conditions-for-main scan designation device;
   a detection device for detecting radiation irradiated from said radiation tube and transmitted through the subject, said detection device comprising a plurality of detection elements arranged in an array form; and
   an image reconstruction device for reconstructing the time-sequentially continuous plurality of images of the subject from the projection data items of the single main scan, said image reconstruction device configured to reconstruct a first image of the time-sequentially continuous plurality of images with respect to a blood flow of the subject based on time-sequential information and a second image of the time-sequentially continuous plurality of images with respect to the blood vessel of the subject using the projection data items obtained during the single main scan.

2. The radiography apparatus according to claim 1, wherein said image reconstruction device is further configured to:
   reconstruct the first image using projection data items obtained during a first scan period within the single main scan; and
   reconstruct the second image using projection data items obtained during a second scan period within the single main scan.

3. The radiography apparatus according to claim 1, wherein said conditions-for-main scan designation device designates the conditions for the single main scan to obtain information with respect to the blood flow and the blood vessel of the subject using the single main scan that is started after the contrast medium is injected into the blood vessel of the subject.

4. The radiography apparatus according to claim 3, wherein said conditions-for-main scan designation device designates conditions of a first scan period within the single main scan for scanning the subject with a first tube current having a first tube current value transmitted to said radiation tube, and designates conditions of a second scan period within the single main scan for scanning the subject with a second tube current having a second tube current value transmitted to said radiation tube, the second tube current value greater than the first tube current value, wherein the conditions of the first scan period include conditions for obtaining information with respect to the blood flow of the subject and the conditions of the second scan period include conditions for obtaining information with respect to the blood vessel of the subject.

5. The radiography apparatus according to claim 4, wherein said conditions-for-main scan designation device designates a time period from a start time of the single main scan to a first time after the start time as the first scan period, and designates a time period from the first time to a second time after the first time as the second scan period.

6. The radiography apparatus according to claim 5, wherein said conditions-for-main scan designation device designates a time period from the second time to a third time after the second time as the first scan period, designates a time period from the third time to a fourth time after the third time as the second scan period, and designates a time period from the fourth time to a fifth time after the fourth time as the first scan period.

7. The radiography apparatus according to claim 4, wherein said conditions-for-main scan designation device designates a timing for switching of the first scan period and the second scan period before performing the single main scan, the timing based on CT values of an image obtained from a monitor scan for monitoring the contrast medium in the blood vessel of the subject.

8. The radiography apparatus according to claim 1, wherein the single main scan is performed using a cine scan mode.

9. The radiography apparatus according to claim 1, wherein the first image comprises a plurality perfusion images including information on at least one of a cerebral blood flow, a cerebral blood volume, and a mean transit time.

10. The radiography apparatus according to claim 1, wherein the second image comprises a three-dimensional image.

11. A radiography method for reconstructing a time-sequentially continuous plurality of images of a subject using projection data items of the subject produced by performing a single main scan for irradiating a radiation to the subject and detecting the radiation transmitted through the subject, said method comprising:
   performing the single main scan after a contrast medium is injected into a blood vessel of the subject, the single main scan producing the time-sequentially continuous plurality of images at one position; and
   reconstructing a first image of the time-sequentially continuous plurality of images with respect to a blood flow of the subject based on time-sequential information and a second image of the time-sequentially continuous plurality of images with respect to the blood vessel of the subject using the projection data items obtained by the single main scan.

12. A radiography method according to claim 11, wherein reconstructing the first image and the second image further comprises:
   reconstructing the first image using projection data items obtained during a first scan period within the single main scan; and
   reconstructing the second image using projection data items obtained during a second scan period within the single main scan.

13. A radiography method according to claim 11, wherein performing the single main scan further comprises performing the single main scan in a cine scan mode.

14. A radiography method according to claim 11, wherein reconstructing the first image further comprises reconstructing a plurality perfusion images including information on at least one of a cerebral blood flow, a cerebral blood volume, and a mean transit time.

15. A radiography method according to claim 11, wherein reconstructing the second image further comprises reconstructing a three-dimensional image.

16. A radiography method according to claim 11 further comprising designating conditions for the single main scan to obtain information with respect to the blood flow of the subject and the blood vessel of the subject during the single main scan.

17. A radiography method according to claim 16, wherein designating conditions further comprises:
   designating conditions of a first scan period of the single main scan for scanning the subject with a first tube current having a first tube current value transmitted to said radiation tube; and
   designating conditions of a second scan period within the single main scan for scanning the subject with a second tube current having a second tube current value transmitted to said radiation tube, the second tube current value greater than the first tube current value, wherein the conditions of the first scan period include conditions for obtaining information with respect to the blood flow of the subject and the conditions of the second scan period include conditions for obtaining information with respect to the blood vessel of the subject.

18. A radiography method according to claim 17, wherein designating conditions of the first scan period further comprises designating a time period from a start time of the single main scan to a first time after the start time as the first scan period, and wherein designating conditions of the second scan period further comprises designating a time period from the first time to a second time after the first time as the second scan period.

19. A radiography method according to claim 18, wherein designating conditions of the first scan period and designating conditions of the second scan period further comprises:
   designating a time period from the second time to a third time after the second time as the first scan period;
   designating a time period from the third time to a fourth time after the third time as the second scan period; and
   designating a time period from the fourth time to a fifth time after the fourth time as the first scan period.

20. A radiography method according to claim 17, wherein designating conditions of the first scan period and designating conditions of the second scan period further comprises designating a timing for switching of the first scan period and the second scan period before performing the single main scan, the timing based on CT values of an image obtained from a monitor scan for monitoring the contrast medium in the subject.

* * * * *